US006463156B1

(12) United States Patent
Gaudriot et al.

(10) Patent No.: US 6,463,156 B1

(45) Date of Patent: Oct. 8, 2002

(54) ACTIVE DEVICE FOR ATTENUATING THE INTENSITY OF SOUND

(75) Inventors: Lionel Gaudriot, Dommartin; Jacques Martinat, Caluire, both of (FR)

(73) Assignee: Comptoir de la Technologie (FR)

(*) Notice: Subject to any disclaimer, the term of this patent is extended or adjusted under 35 U.S.C. 154(b) by 145 days.

(21) Appl. No.: 09/687,441

(22) Filed: Oct. 13, 2000

(30) Foreign Application Priority Data

Oct. 18, 1999 (FR) ........................................ 99 13164

(51) Int. Cl.[7] ........................................ A61F 11/06

(52) U.S. Cl. ........................................ 381/71.1

(58) Field of Search ........................................ 381/71.1, 71.3, 381/71.4, 71.7, 94.1

(56) References Cited

U.S. PATENT DOCUMENTS 5,315,661 5/1994 Gossman et al.

5,438,624 8/1995 Lewiner et al.

FOREIGN PATENT DOCUMENTS

| | | |
|---|---|---|
| DE | 2139941 | 3/1973 |
| DE | 3922185 | 1/1991 |
| EP | 0787340 | 8/1997 |
| JP | 60150399 | 8/1985 |

OTHER PUBLICATIONS

Bolton et al, "Sound Cancellation by the use of Secondary Multipoles", Journal of the Acoustical Society of America, US, American Institute of Physics, New York, vol. 98, No. 4, (1995).

*Primary Examiner*—Minsun Oh Harvey

(74) *Attorney, Agent, or Firm*—Wall Marjama & Belinski LLP

(57) ABSTRACT

An active device for attenuating noise in a defined region using anti-noise waves. Sensors capable of detecting noise waves and the direction of the waves and providing data to a processor for controlling an electro-acoustic source so that the source emits anti-noise waves in a direction counter to the direction of the incoming noise waves.

8 Claims, 7 Drawing Sheets

ACTIVE DEVICE FOR ATTENUATING THE INTENSITY OF SOUND

TECHNICAL FIELD

The invention relates to the field of acoustics. More specifically, it is aimed at fixed devices for attenuating the noise generated by moving sources, especially such as transportation means in general and aircraft or land transport in particular.

The invention constitutes an improvement of the device described in the Applicant's patent EP 0,787,340.

PRIOR ART

The Applicant has described in the aforementioned patent a device for attenuating the intensity of sound which operates on the principle of the emission of an antinoise wave generated on the basis of information coming from sensors and emitted by electroacoustic sources placed in such a way that the antinoise waves combine with the noise waves that they admit as envelope.

The principles described in that patent remain valid for the present improvement so that said document is cited here as a reference, and its content will therefore not be explained in detail below.

In the embodiments illustrated in that document, the various antinoise sources are combined by subassemblies mounted on vertical masts, that is to say in a direction approximately perpendicular to the mean direction of incidence of the noise waves.

In that document, the various masts are placed near the region to be protected and preferably around the periphery of the region to be protected.

However, it has been found that the separation of the masts as described in that document does not allow the sound waves having a relatively high frequency, and especially greater than 500 Hz (hertz), to be sufficiently attenuated.

One problem that the invention aims to solve is that of the effective attenuation of sound waves lying in a range up to one kilohertz, or even up to 2 kHz (kilohertz).

SUMMARY OF THE INVENTION

The invention therefore relates to an active device for attenuating the intensity of sound in a defined region, by the emission of antinoise waves, of the type comprising:

- a set of sensors capable of determining the signals and the directions of the waves emitted by remote noise sources;
- means for processing the signals coming from said sensors and for generating signals corresponding to the antinoise waves;
- a set of electroacoustic sources, said sources being installed in the space close to the region to be protected and connected to said processing means and being capable of emitting antinoise waves in the same direction and in the same sense as the incident waves, the sensors and the electroacoustic sources being placed in such a way that the incident waves reach the sensors beforehand.

This device is distinguished in that the electroacoustic sources are arranged on a continuous surface and in a uniform lattice.

In other words, the invention consists in combining the various sources in such a way that they constitute a lattice close enough to allow attenuation of the high-frequency waves, that is to say in the application to the treatment of sound waves of the order of one kilohertz in frequency.

Thus, according to one characteristic of the invention, the sources are spaced apart from the region by a distance of between one and two meters.

It may be readily appreciated that the use of masts as described in the aforementioned document would be completely unrealistic for covering a frequency range going up to one kilohertz, since it would result in much too high a mast density on the ground.

This is because, according to one theory on the operation of active screens, it seems that the monolayer continuous screening effect is limited in the frequency range because of the discrete distribution of these sources over the surface. What is involved is a low-pass phenomenon whose cutoff frequency is: $f_0=\alpha c_o/a$, where:

- a denotes the characteristic dimension of the source lattice cell;
- $\alpha$ is a parameter slightly greater than 1, characteristic of the geometrical shape of the cell; and
- $c_0$ is the speed of sound.

Above this cutoff frequency, the incident waves are no longer only reflected by the screen but also diffracted upstream and downstream of the screen, with the effect of inducing a pressure level twice the level of the incident wave, which then makes said screen not only inoperative but also disruptive.

The choice of a sufficiently close lattice cell, of the order of magnitude of half a meter, makes it possible to obtain a cutoff frequency of the order of one kilohertz encompassing most of the power spectrum of the sound wave from an airplane, for example.

Thus, the various sources are arranged over surfaces which may be formed by a lattice which is itself raised up, placed above the region to be covered or above the buildings which adjoin said region.

The term "continuous surface" should be understood to mean a surface which exhibits geometrical regularity such that all the sources may be regarded, with respect to a noise wave, as equivalent in their contribution to the attenuation, to within the effect of their orientation.

Such surfaces may be plane, or else, for example, belong to the family of quadrics, especially cylinders.

In practice, it has been found that a hexagonal lattice allows the sources to be most compact and therefore achieves the best coverage within a frequency band for the same source density.

According to another characteristic of the invention, the device according to the invention comprises several sets of electroacoustic sources arranged over several surfaces offset one with respect to the other by translation normal to their surface, so as to form multilayer complex electroacoustic sources, thereby increasing their transverse spacing for the same bandwith.

Thus, when the loudspeakers, which form the electroacoustic sources, are combined on surfaces which are close together and more or else parallel, these combinations of loudspeakers have the effect of one loudspeaker of larger cross section, without occupying the area thereof.

This is because a single loudspeaker of identical working area would occupy too high a proportion of the lattice, which in turn would reduce the visual transparency of the screen.

In particular configurations, several devices may be combined in such a way that these devices are juxtaposed beside one another in the space of the region to be protected in order to cover one particular geometrical region such as, for example, a crossroad. These devices may be combined so as to be continuous with surfaces of the same type forming passive screens, especially glazed structures, for architectural and functional reasons.

The various screens are driven by a microphonic pickup system located closely upstream of the screen. This noise wave pickup system has the ability to separate and characterize these waves, in terms of direction and of signal respectively, so as to allow the antinoise sources to counteract them additively.

In the case of a single noise source, all the echoes carry practically the same signal, namely that of the direct wave. This is therefore the signal of the first wave picked up with an amplitude factor and a time delay.

The control means are capable, using the appropriate algorithms, of extracting the common reference signal, together with the amplitude and delay parameters specific to each echo signal, from a set or from a base of microphonic sensors placed upstream of the screens.

The minimum number of sensors to be used in the microphonic base is at least equal to the number of signals to be discriminated, but, in practice, this number is greater in order to overcome the effect of parasitic noise of nearby origin.

In more complex situations, the noise sources are multiple and independent sources such as, for example, in the case of noise generated by land transport means such as vehicles, automobiles or trucks.

In this case, the number of specific signals, which are independent sources, is more than about ten. Many complementary directional microphonic bases will then be used, these preferably being arranged as close as possible to the sources.

For example, the microphonic bases may be arranged along the highway or along the railroad track for selective acquisition, by proximity of the various reference signals specific to the independent sources, such as wheel trains, bogies and aerodynamic boundary layers.

Consequently, the separation of the various noise waves at the screen is facilitated by prior knowledge.

However, in this case the signals which propagate from the microphonic base to the screens are subject to the vagaries of the atmospheric propagation of sound, which must be taken into account in the algorithms for separating the signals in the microphonic base close to the screen.

In all cases, the algorithm principles used for signal selection require great accuracy. This accuracy of the algorithms is determined by the overall accuracy of reconstruction of the antinoise waves, which is evaluated in the following manner.

Assuming that the active screen is intended to oppose a noise wave of amplitude n(t), by generating an antinoise wave of amplitude an(t), the amplitude of the residual noise is e(t)=a(t)−an(t). The quadratic norm, or its energy evaluated over the time characteristic of the auditory perception of the noise signals (about one tenth of a second) is as follows: $\overline{e^2}=\overline{n^2}-2\overline{an.n}+\overline{an^2}$, where the bar above the symbols denotes the time-averaging effect.

The attenuation factor $A_u=\overline{e^2}/\overline{n^2}$ is expressed by the following formula:

$$A_u=2r(1+M/2)+(1-r)M_2/4$$

in which:

r is the defect coefficient at the unit of correlation of the n(t) and an(t) signals, which is given by the following formula:

$$1-r=\overline{a.an^2}/\sqrt{\overline{n^2}.\overline{an^2}};\text{ and}$$

M is the ratio of the energies, according to the following formula:

$$1+M=\overline{an^2}/\overline{n^2}.$$

In order to obtain an attenuation factor of the order of 20 decibels, it is therefore necessary for the antinoise signal/noise signal correlation coefficient to be 0.995, which value demonstrates the very great similarity to be obtained between broadband noise signals.

This value means overall that the various elements involved in the attenuation device must have a quadratic accuracy of the order of $2\times10^{-3}$, not achieved in the field of standard sound reproduction.

BRIEF DESCRIPTION OF THE INVENTION

The way in which the invention is realized and the advantages which stem therefrom will become clearly apparent from the description of the particular embodiments which follow, supported by the appended figures in which.

THE MANNER OF REALIZING THE INVENTION

As already stated, the invention relates to an improvement of the noise attenuation device as described in patent EP 0,787,340.

Such a device comprises a certain number of surfaces combining electroacoustic sources. According to one characteristic of the invention, these surfaces are continuous so as to cover an area that may range up to several hundred square meters, these surfaces being placed at heights of about 10 to 15 m, or higher, above the places to be protected.

These surfaces are produced, for example, by a lattice of tubes or of cables, at the intersection of which the antinoise sources are fixed.

Figure 1:
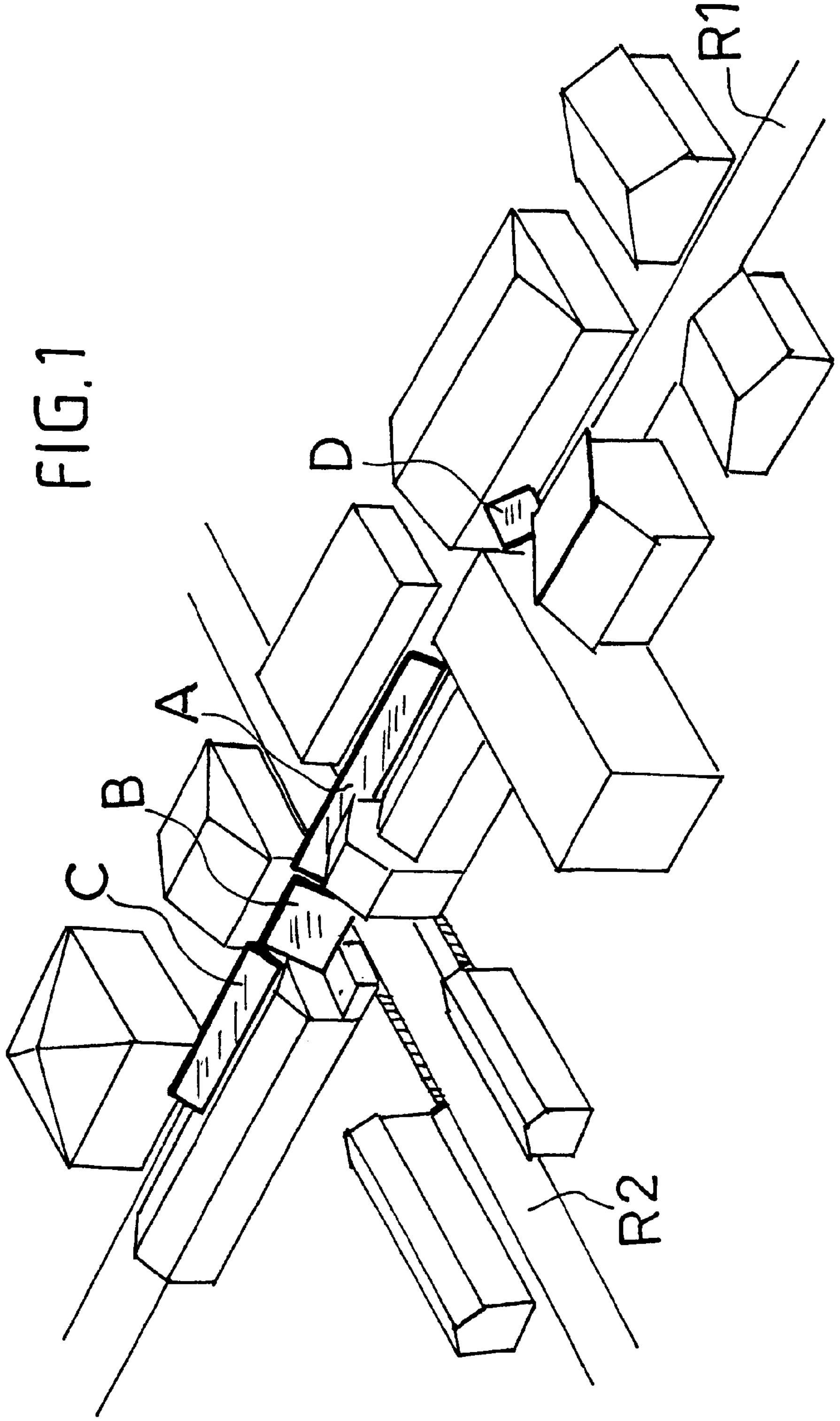
FIG. 1 is a schematic perspective view of a habitation region provided with several screens according to the invention.

As may be seen in FIG. 1, the region to be protected may comprise a number of flat screens A, B, C, D intended to provide this protection.

The screens A, B, C are placed above the street to be protected R1, whereas the screen D is placed, at a certain height, across the street R1 and is intended to block the guided waves by multiple reflections off the facades along the street.

In the particular case in FIG. 1, the device makes it possible to protect part of the urban area adjacent to an airport from the noise of airplanes taking off and landing along a path approximately parallel to the street R1, illustrated in FIG. 1, at a horizontal distance of about half a kilometer.

More specifically, the screens A and C are placed immediately above the building facades, facing the region to be protected. They are arranged in such a way as to be inclined with respect to the vertical.

As regards the screen B, this is placed across a street R2 perpendicular to the main street R1 parallel to the path of the airplane. This screen B closes the gap offered to airplane noise when it overhangs this perpendicular street R2.

As regards the screen D, this is placed in the same way, across the street R1, so as to reflect the noise which reaches the region to be protected, in a guided manner by prior multiple reflection along the facades in the street R1.

The screens B and D are also inclined in order to improve the effectiveness of the attenuation device.

Figure 2:
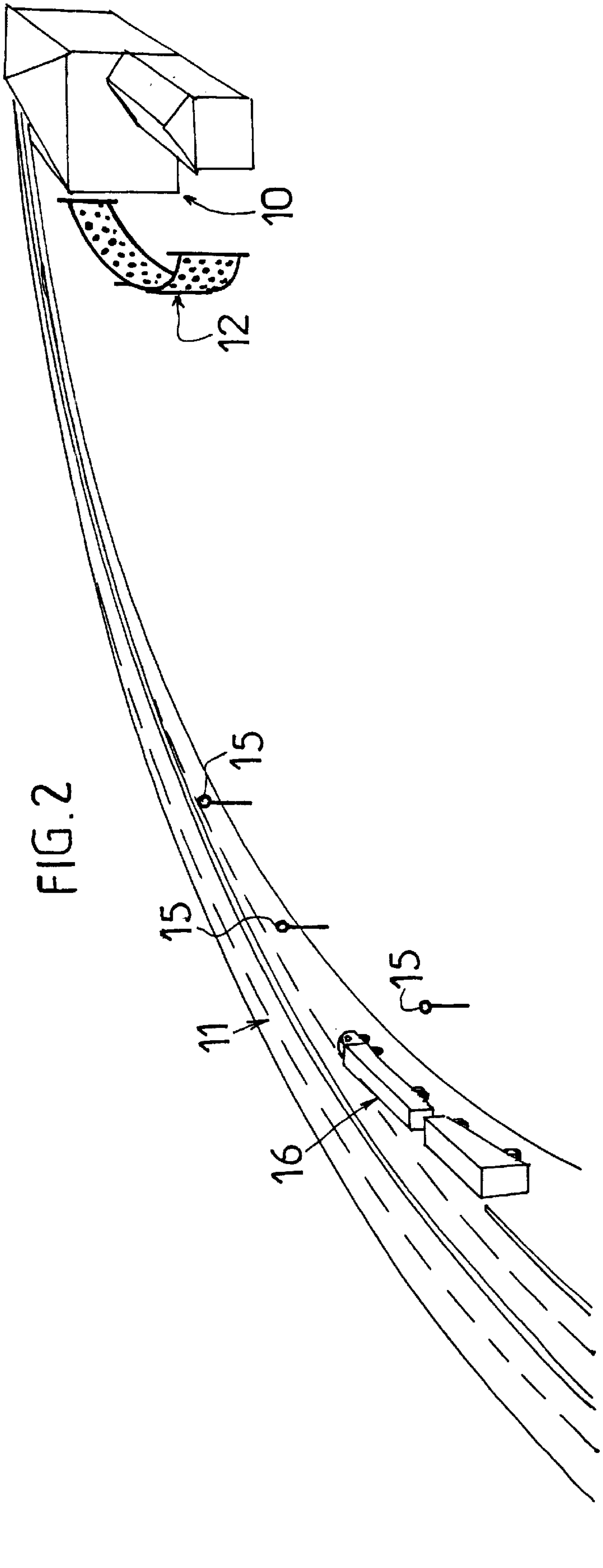
FIG. 2 is a schematic perspective representation of a habitation located near a highway and provided with screens according to the invention.

In another embodiment, as illustrated in FIG. 2, the device is intended to protect an isolated dwelling (10) bordering a freeway route (11) from the traffic noise.

More specifically, the device consists of a cylindrical screen (12) suitable for protecting the main facade of the dwelling (10) exposed to the noise.

FIG. 2 also shows the presence of a plurality of microphones (15) placed along the immediate edge of the highway (11) and intended to pick up the actual noise from the vehicles (16).

The signals generated by the microphones (15) are sent to the unit for driving the screen (12) via a suitable means and especially by a wire link (not shown).

As shown, the screens consist of pylons (20–22) of suitable shape supporting panels (24) in the form of a regular lattice having triangular, square or preferably hexagonal lattice cells, at the center of which the antinoise sources (25) are fixed. These sources may be single layers or preferably multilayers, that is say consisting of a combination of several loudspeakers offset with respect to one another along the normal to their reference surface.

Figure 3:
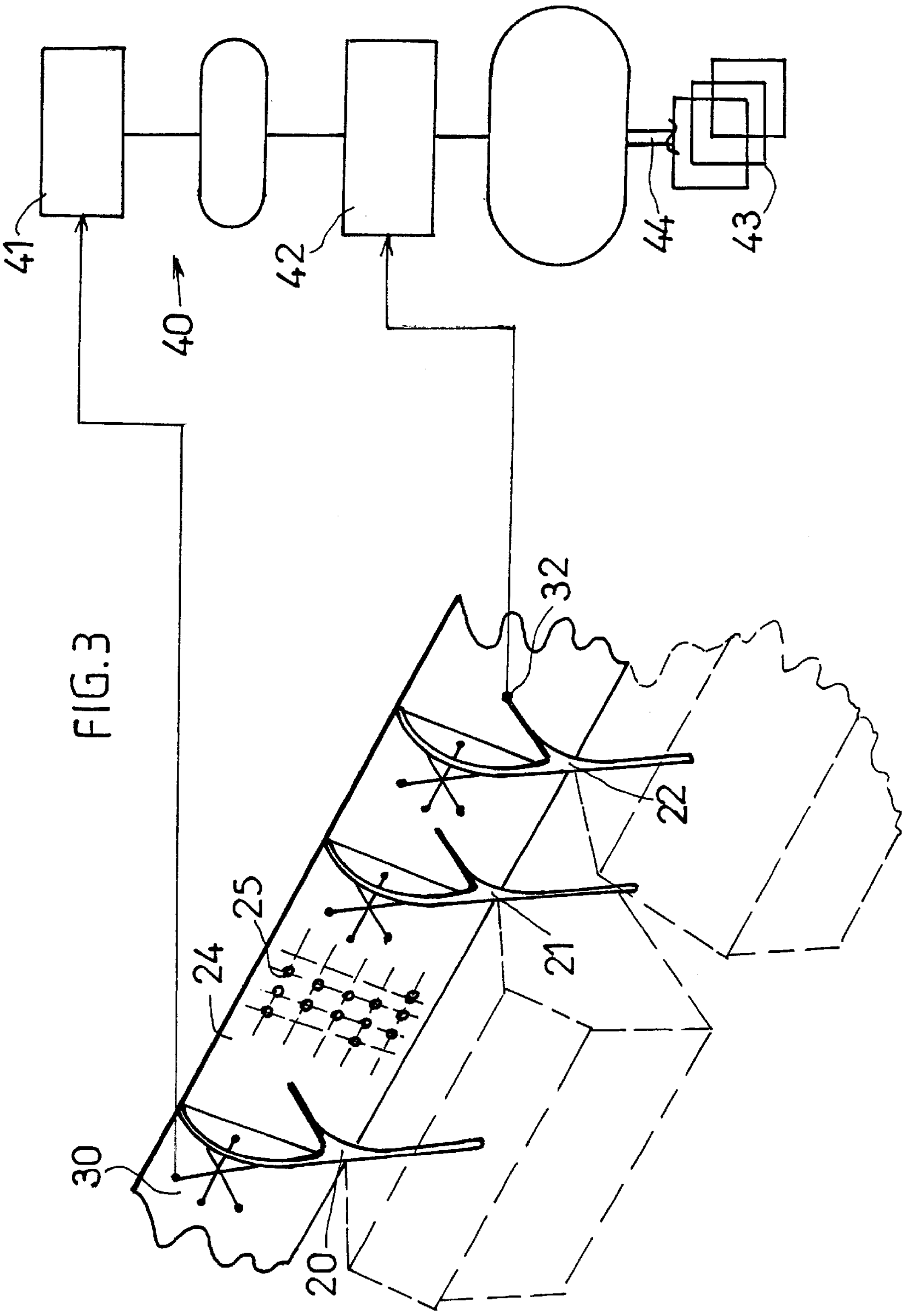
FIG. 3 is a schematic representation of a screen according to the invention together with various units for controlling each of the active elements of the screen.

As shown in FIG. 3, associated with each panel (24) is a microphonic pickup base (30) and an electronic control system (40) which comprises the following functional units:

an antinoise wave characterization unit (41);

an antinoise source control unit (42);

integrated control units (43).

More specifically, the noise wave characterization unit (41) is used to determine the main characteristics of the direct incident waves and those reflected by the ground and various obstacles.

This characterization unit (41) determines the respective directions of the normals to these waves, the acoustic signals specific to each of them and their relative positions over time.

The delay of each of these signals with respect to the direct wave signal is determined with respect to a single reference point Oi, called "reference point of the microphonic base", generally located at its barycenter.

The antinoise source control unit (42) carries out identical linear filtering for each of the characteristic signals of the noise waves coming from the aforementioned characterization units (41).

The purpose of this filtering is to equalize the electroacoustic source group times over the range of the active frequency band of the screen.

Each of the filtered signals is then sent, for example by multiplexing, over a common bus (44) to the integrated antinoise source control units (43).

At the same time, and in a sequenced manner, the characteristic delays of the signals are also transmitted over this bus (44). These delays are continuously changing according to the movement of the noise source, and with the vagaries of the sound propagation.

Each antinoise source is itself provided with its own integrated control unit (43), the function of which is twofold, namely:

to position in time the signals specific to the various waves, by applying to them, via adjustable "delay lines", the delays which correspond to their geometrical position. Thus, the antinoise sources must deliver signals in strict concomitance with those that the various waves sweeping over their active surfaces carry. The delays are calculated from the reference delays transmitted over the bus, according to the geometrical position of the source with respect to the reference point of the microphonic base M;

to sum all the signals thus readjusted over time;

to apply them, after digital-analog decoding, to amplifiers specific to each elementary antinoise source.

The antinoise sources located on the perimeter of the screens are subjected to control signals which are similar overall but are adjusted in a particular manner in terms of level and delay in order to regularize the edge effects.

Moreover, it is advantageous to place, within the volume lying downstream of the screen, that is to say under its acoustic protection, one or more residual noise monitoring microphones (32), the signals from which are returned to the antinoise source control unit (42) so as to fulfill complementary functions such as:

the supervision of the local operation of the system with permanent adjustment by a feedback loop, having a time constant of a few seconds, making it possible to palliate the parametric drifts and thus ensure the best conformity of the antinoise acoustic signals with respect to the noise signals;

the fine adaptive adjustment of the antinoise source control laws, particularly for the contour sources, with respect to edge effects of the screens as a function of the movement of the airplane, with a time constant of the order of one second;

the detection of operational anomalies with the possibility of shutting down the system and an indicating means;

the possibility of carrying out automatic test procedures.

As explained above, in order to obtain a good attenuation performance of about 20 decibels, it is necessary for the overall accuracy of the measurement and reconstruction system to be $5\times10^{-3}$ in terms of linearity, thereby requiring an accuracy on each component of the system of about $2\times10^{-3}$.

Consequently, with regard to the antinoise sources, namely the various loudspeakers and associated analog amplifiers, the degree of nonlinear distortion must be less than $2\times10^{-3}$ at the maximum level delivered.

This accuracy requirement demands particular attention with regard to the design of the loudspeakers and of their control circuits.

With regard to the microphones which form the pickup base for the various noise waves, the effects of the physical parameters relating to the environment, such as temperature, atmospheric pressure and relative humidity, are compensated for so as not to affect the linearity of the response above the $2\times10^{-3}$ level required.

The effects of wind on the microphones, having a short time constant, typically less than one second, are limited aerodynamically using, for example, profiled porous bodies as protective envelopes and electronically in order not to disturb the antinoise control signals in the operational frequency band of the system.

With regard to the unit (41) for characterizing the signals specific to the incident waves to be treated by the screen, the accuracy and the extraction of the signals must be of the order of $10^{-3}$, which means, in particular, an amount of crosstalk less than this value, and thus fixes the overall performance of the algorithms designed to carry out this discrimination in real time.

Apart from the requirements regarding the linearity of the various processing components, one particular requirement is that for the temporal adjustment resolution of the antinoise source control signals, necessary for ensuring that they are concomitant with the noise wave signals, and therefore an inverse function of the high-frequency limit of the operating bandwidth of the system.

More specifically, to obtain the 20 decibel attenuation level, it has been found that it is necessary for the antinoise signal-noise signal correlation coefficient to be greater than 0.995, which means a maximum phase shift between their spectral components of 6°, i.e. $1/60^{th}$ of a period.

It follows that the temporal resolution of the signals must typically be better than 17 microseconds for a frequency of one kilohertz.

Thus, the clock rate which fixes the temporal signal adjustment step in the loudspeaker control units will be greater than 60 kilohertz. Translated into a wavelength, this temporal resolution corresponds to a geometrical positional resolution of one sixtieth of the maximum wavelength, i.e. 5 mm for a maximum frequency of 1 kilohertz.

This value corresponds to the requirement on the rigidity of the support structure which links the microphonic base to the panel of antinoise sources.

Its deformation, especially under the wind loading, must therefore not cause relative displacements greater than this value, in order to maintain an attenuation level of the order of 20 decibels.

The operation of the antinoise active screen as a device for attenuating sound waves in free space is already described in the Applicant's patent EP 0,787,340. This is therefore a similar system of antinoise sources, designed and driven signalwise in order to generate antinoise waves algebraically opposed to the tangent noise waves.

For a clearer understanding of the operation of the invention, it may be useful to give a direct and effective physical description of the operation, explaining the necessary spatial and temporal concomitance with regard to the antinoise sources.

Thus, regarding an incident wave reaching the system in the fundamental form of a noise wavefront, that is say a particulate acceleration jump, to be linearly filtered within the useful frequency band, the action of the antinoise sources with respect to this wavefront consists, for each source, in interacting with this wavefront at the precise instant of its passage, in such a way that this wavefront does not propagate beyond the source toward the downstream region to be protected.

The antinoise sources therefore create, in concomitance, boundary conditions suitable for reflecting or absorbing the incident wavefront. The antinoise sources thus constitute screens producing, in acoustic terms, particular boundary conditions.

If these antinoise sources consist of electrodynamic loudspeakers, they behave of course, within the frequency range in which they are used, as sources having a variation in acoustic output.

Corresponding to the current injected into the coil of the loudspeaker is a Laplace force which encounters, as main reaction, the inertia force of the moving component of the loudspeaker. This moving component undergoes an acceleration proportional to said current.

The control system controls this acceleration and therefore the variation in acoustic output delivered by the loudspeaker membrane and, concomitantly, at twice the normal output of the acoustic noise wave over the surface of the cell specific to the loudspeaker, this antinoise source producing, over said cell, a boundary condition for total reflection of the wave.

The pressure on the surface of the screen is in fact zero, and the acoustic load on the source is therefore zero.

This is the theoretical mode of operation of an active screen consisting of a single layer of loudspeakers. However, as already mentioned, such a mode of operation with a single source has a cutoff frequency which is not high enough to counteract the annoying part of the spectrum of waves emitted by conventional transportation means insofar as the surface density of the loudspeakers is limited in order to preserve the visual transparency of the screen.

Figure 4:
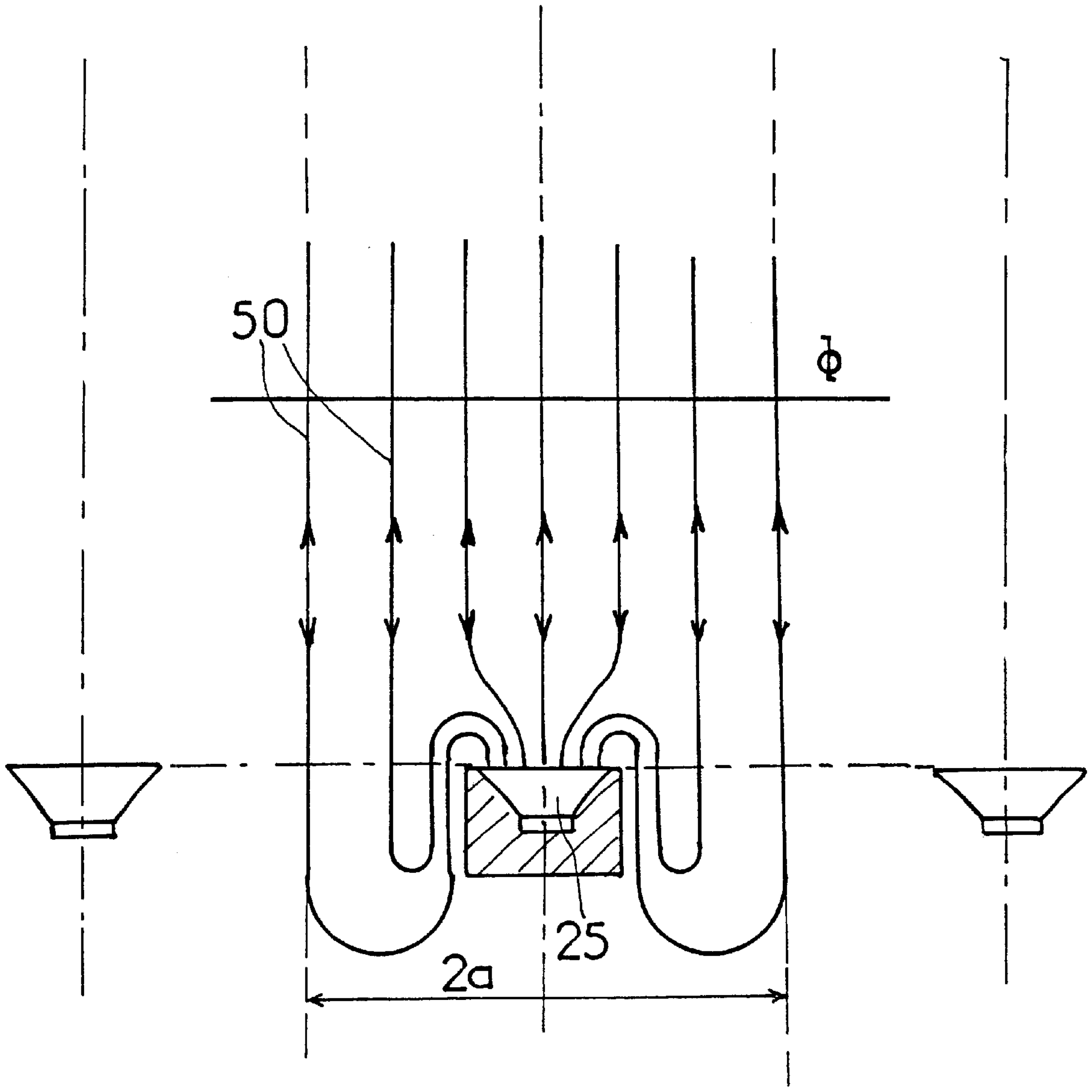
FIG. 4 is a schematic representation of a monolayer electroacoustic source used in a screen according to the invention, in one cell of the grating.

In fact, and as illustrated in FIG. 4, it has been found that an interference field is established between the incident noise wave and the wave reflected by the sources, in the vicinity of these said sources, the "lines of current" (50) of which interference field are shown schematically by the tangents at each point to the major principal axis of the acoustic particulate hodographs.

This field is organized spatially as a grating, by tubular cells which are repeated periodically according to the lattice cells of the screen, as soon as these lattice cells are sufficiently numerous, in order for the organization of the interference field to be almost invariant from one lattice cell to another.

In each tubular cell, the "lines of current" make it possible to define tubes of acoustic current which converge on the active surface of the antinoise source, that is to say the membrane of the loudspeaker (25).

These tubes constitute as many imaginary waveguides within which the interference field is established.

The diagram in FIG. 4 is used to illustrate the following phenomena.

In fact, compared with the reference phase wave surface $\phi$, the path difference of the guided waves increases as the tubes get further away from the axis of revolution, becoming virtually equal to the diameter "a" of the cell.

The cutoff phenomenon occurs for: $\lambda_0/2=c/2f_0=a/2$ when the steady state along the outermost tube has a half-wavelength of the path difference with respect to the central tube, and is therefore in phase opposition with the output of the antinoise source.

The cutoff frequency $f_0$ is therefore close to c/a, as mentioned above.

Above this frequency, the incident traveling wave guided in the outermost tube can no longer be controlled by the antinoise source and it passes through the screen, giving rise to oblique refracted waves which encumber the protective role conferred on the screen.

Figure 5:
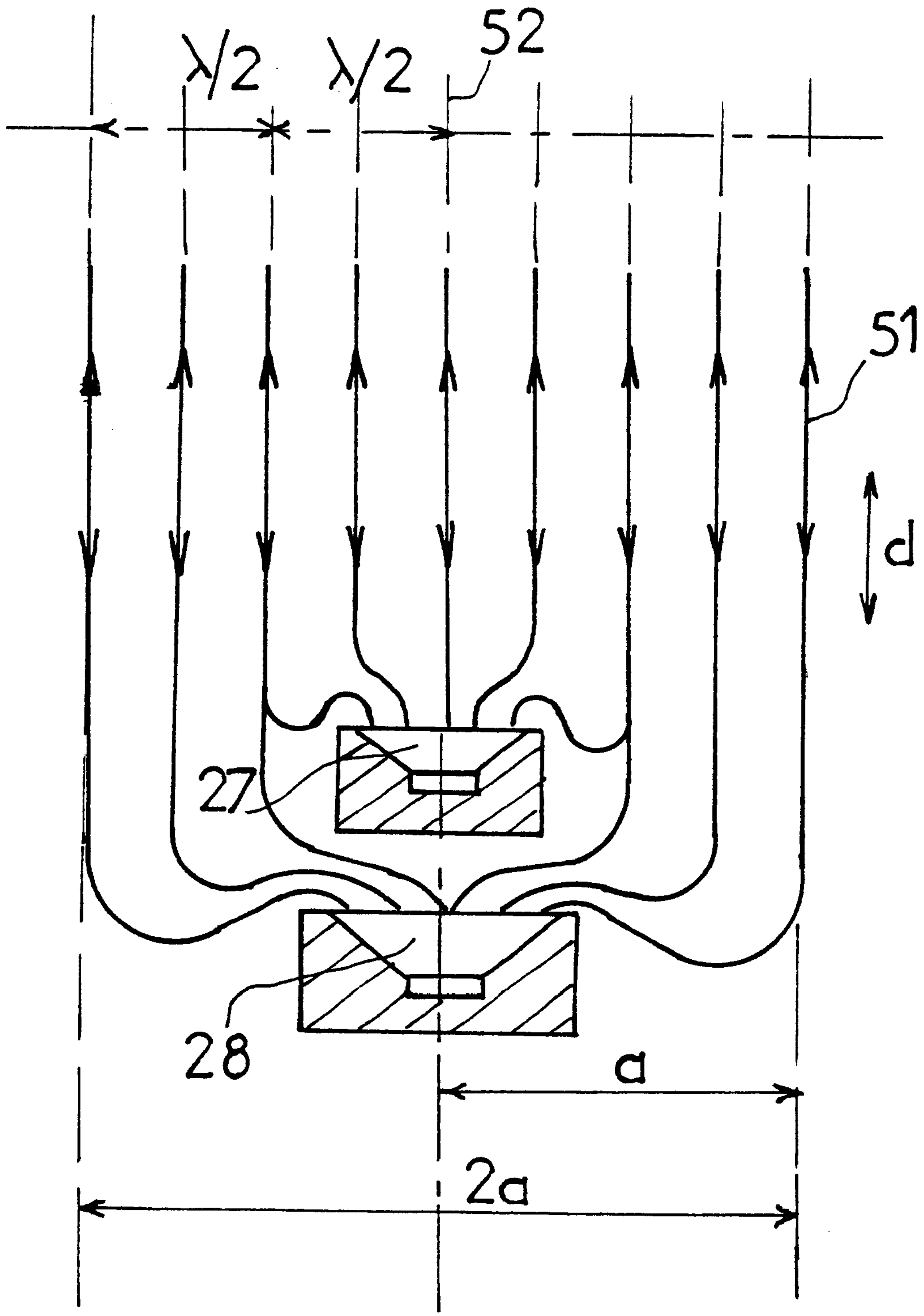
FIG. 5 is a schematic view illustrating a two-layer combination of sources. In the last two figures, the lines tangential to the longest principal axis of the acoustic particulate hodographs have been plotted.

According to another characteristic of the invention, the sources may advantageously be arranged in subassemblies as mutually parallel screens, and the operation is then as illustrated in FIG. 5.

In fact, the operation of multilayer sources makes it possible to increase the cutoff frequency of the system for a given size of the grating cell. More specifically, and as per the diagram illustrated in FIG. 5, the various sources (27, 28)

of the same cell are driven, with a predetermined phase shift, in order to act on the outermost tube (51) so as to prevent it from escaping above the frequency $f_0$ by continuing to ensure that the "lines of current" remain channeled toward the source in the appropriate layer.

In fact, and as referenced in FIG. 5, along the axis (52) of the sources (27, 28) and therefore under the first source (27), a series of secondary sources (28), driven with the desired phases and moduli makes it possible to pick up and reflect the acoustic output of the incident wave, for lines of current which escape the first source (27), by complying with the interferential structure of the acoustic field, close to the loudspeaker, as described above.

For simplification, FIG. 5 shows a single secondary source.

On the lines of current plotted, there is a path delay in order to reach the second source (28) of the order of d+a, where d represents the distance between the membranes of the loudspeakers (27, 28) and a is the half-cell of the screen.

According to the invention, this path delay is compensated for by the drive device, which feeds this second source (28) with a signal delayed by approximately (d+a)/c, this value being able to be adjusted with greater precision, so as to ensure strict orthogonality of the source field to the oblique modes of the grating.

The cutoff frequency is thus increased to twice the initial frequency, which is itself about c/a.

In this context, the outputs of the sources are adjusted in proportion to the surfaces of the current tubes controlled.

The principle may extend to a greater number of sources and the table below gives the cutoff frequency for different numbers of layers of antinoise sources, for two particular surface densities of the sources.

| Number of layers | | 1 | 2 | 3 | 4 |
|---|---|---|---|---|---|
| Cutoff frequency in hertz | One multiple source per 1 $m^2$ | 370 | 700 | 1000 | 1300 |
| | One multiple source per 5 $m^2$ | 170 | 300 | 450 | 600 |

The sources as shown in FIG. 5 by loudspeakers having a common axis may advantageously be produced by contiguous assemblies of smaller-sized sources suitably joined together and driven with the appropriate delays in order to ensure optimum regularity of the acoustic output field.

It is apparent from the foregoing that the device according to the invention attenuates the noise in a frequency band covering most of the noise wave spectrum from transportation means such as airplanes or trains.

The screen described operates as an active reflector with respect to the incident noise waves; however, it is possible to envisage the screen operating as a perfect absorber for these waves insofar as the reflected waves could, in certain situations, have a harmful effect on the surrounding site.

To do this, in theory it is necessary for variable acoustic pressure sources to be combined with the variable acoustic output sources so as to produce, on the surface of the screen, the hybrid matching boundary condition: $\delta p/\delta t=\rho_0 c_0\ \delta V_n/\delta t$, where:

p denotes the acoustic pressure;

$V_n$ denotes the acoustic velocity normal to the screen;

$\rho_0 c_0$ denotes the acoustic impedance of the air.

Both these types of source are driven in concomitance on the basis of the same signals specific to the incident noise waves.

Having practically no acoustic pressure sources means that the same condition has to be achieved on the basis of a double distribution of variable output sources placed on two parallel surfaces separated by a distance e, with e being less than the minimum half-wavelength.

Under these conditions, a simple model shows that by driving the downstream source in quadrature with the incident wave and the upstream source shifted in time by $e/c_0$, with the same amplitude, the required matching condition is obtained over a decade of frequencies using a device for varying the source output about three times higher than for a single screen.

Under such operation, the downstream source is acoustically unloaded and it is the upstream source which absorbs the power of the noise.

Moreover, the active acoustic reflector screens described may be combined in their operation with contiguous passive screens. These passive screens may consist of pre-existing constructed surfaces (roofs and facades of buildings in FIG. 1). They may be installed for acoustic reasons, as a complement to the active screens, and produced according to suitable architectural techniques, especially using glazed surfaces of suitable thickness, according to customary or esthetic arguments specific to the layout of particular sites.

Such passive screens then cause dual-type reflection of the type that is described for the active screens, namely that, being acoustically "hard", they create the boundary conditions approaching cancellation of the normal acoustic velocity and doubling of the acoustic pressure at their surface.

Precautions must be taken at the join between these two types of screen in order to prevent the resulting large pressure gradients from locally impairing the desired specific reflection effects by causing acoustic leakage into the volume to be protected.

The recommendation of the present patent is to soften these gradients by passing more gradually from active control of the "hard" reflective screen type (zero normal velocity) toward that described as a "soft" reflective screen (being characterized by a zero pressure).

To produce a "hard" active screen, sources with pressure variation control are used. These are sources not available a priori; on the contrary, the various types of standard loudspeakers are closer to variable output sources and their response time makes it illusory for them to be controlled in terms of pressure variation.

Such sources are produced by combining, in pairs, opposed variable output sources mounted back to back, forming an acoustic dipole.

In particular, such sources are to be used for producing active screens over apertures in the facades of buildings, windows or openings, so as to fulfill the reflection condition in the "open window" situation, thus preventing the external noise from penetrating the interior of dwellings.

Figure 6:
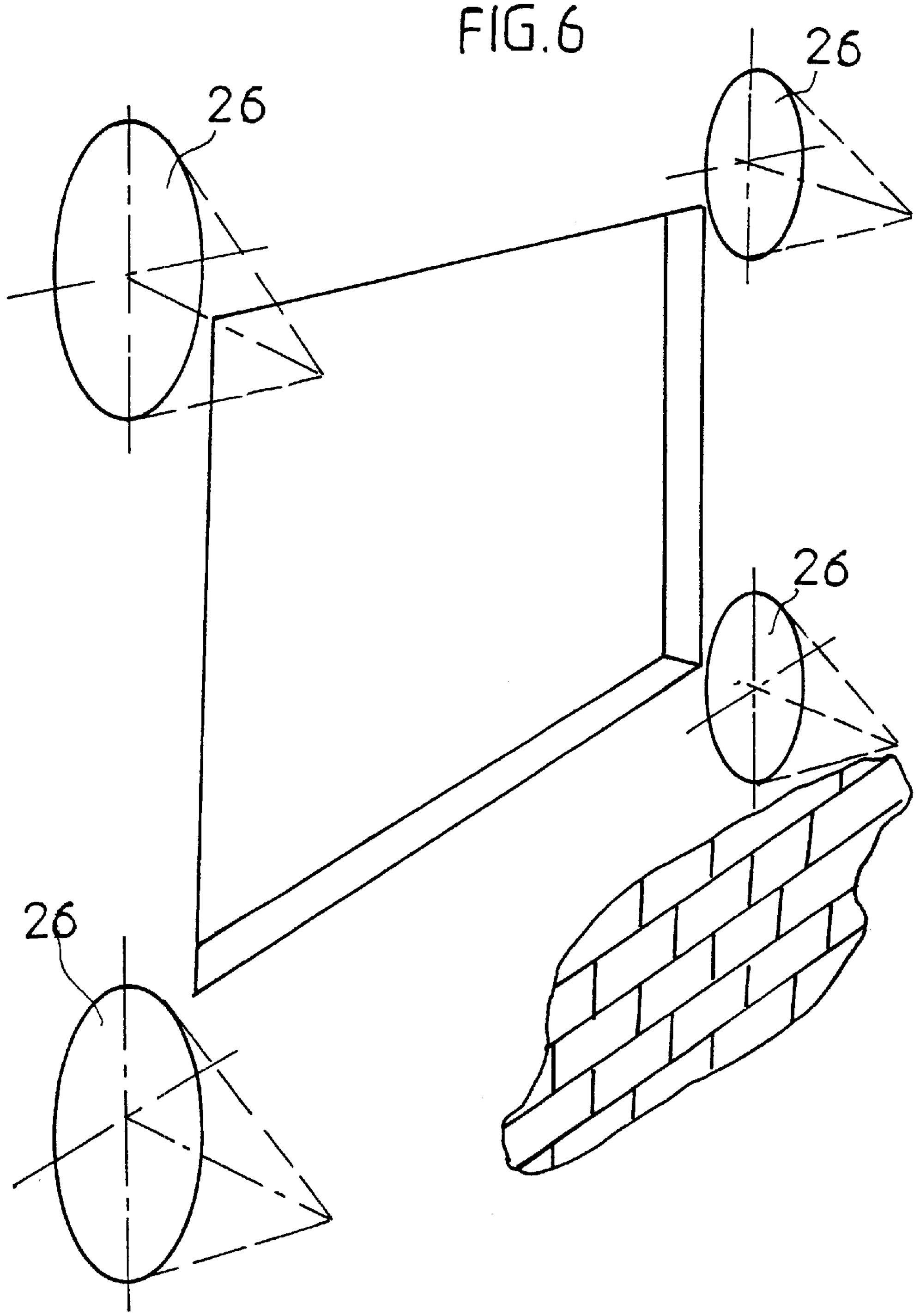
FIG. 6 shows a window reveal protected by a plurality of electroacoustic sources arranged according to the invention.

To do this, multiple bipolar-type sources are produced, for example four sources (26) at the four corners of the reveal, according to the arrangement illustrated in FIG. 6.

Figure 7:
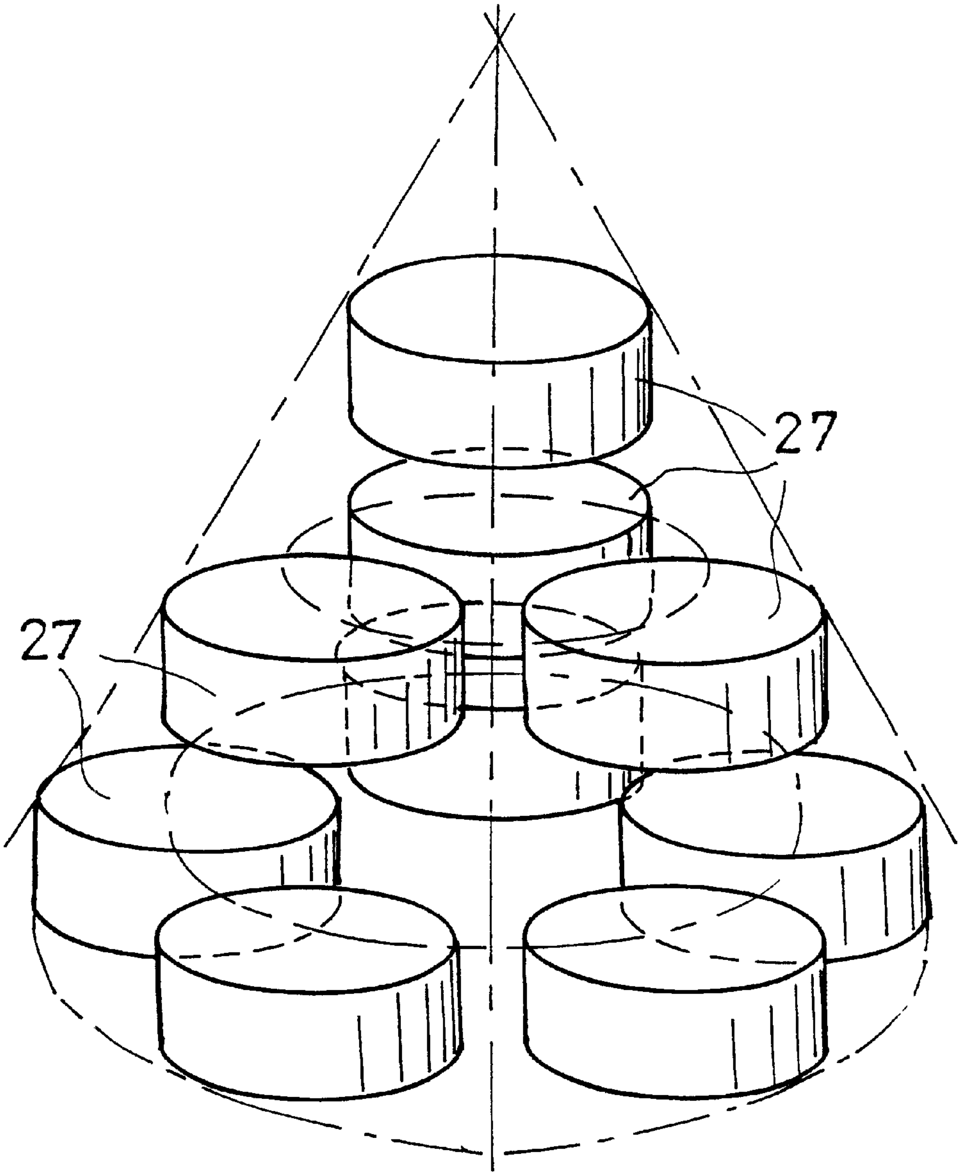
FIG. 7 is a schematic perspective view of a number of sources combined in three parallel planes.

Such multiple sources can be produced, as illustrated in FIG. 7, by the combination of several elementary sources (27) arranged in parallel planes. Each elementary source (27) is a bipolar source having two faces said to be in opposition.

What is claimed is:

1. An active device for attenuating the intensity of sound in a defined region, by the emission of antinoise waves, of the type comprising a set of sensors (30) capable of determining the signals and the directions of the waves emitted by the remote noise sources;

means for processing the signals n(t) coming from said sensors and for generating signals an(t) corresponding to the antinoise waves;

a set of electroacoustic sources (25), said sources being installed in the space close to the region to be protected and connected to said processing means and being capable of emitting antinoise waves in the same direction and in the same sense as the incident waves, the sensors and the electroacoustic sources being placed in such a way that the incident waves reach the sensors beforehand, wherein the electroacoustic sources (25) are arranged on a continuous surface (24) and in a uniform lattice, this surface constituting a screen which is reflective with respect to sound waves, or optionally absorbent with respect to them.

2. The device as claimed in claim 1, wherein the electroacoustic sources (25) are arranged in a hexagonal lattice.

3. The device as claimed in claim 1, wherein the lattice has a pitch of less than two meters.

4. The device as claimed in claim 1, which comprises several sets of electroacoustic sources arranged over several surfaces offset one with respect to the other by translation, along their normal, so as to limit the surface density of the sources for a given high cutoff frequency.

5. The device as claimed in claim 1, wherein the continuous surfaces have a plane geometry or a quadric, especially cylindrical, geometry.

6. The device as claimed in claim 1, which is combined with a rigid structure forming a solid screen.

7. The device as claimed in claim 1, wherein some of the electroacoustic sources are combined in pairs to form acoustic dipoles.

8. A system composed of several devices as claimed in claim 1, wherein the various devices are juxtaposed within the space of the region to be protected.

* * * * *